(12) United States Patent
Bordon et al.

(10) Patent No.: US 11,612,386 B2
(45) Date of Patent: Mar. 28, 2023

(54) UNIVERSAL SURGICAL ACCESS SYSTEM

(71) Applicant: BB Surgical Devices, S.L., Valencia (ES)

(72) Inventors: Gerd Bordon, Valencia (ES); Fernando Vicente Beltrán Guinart, Valencia (ES)

(73) Assignee: BB Surgical Devices, S.L., Valencia (ES)

( * ) Notice: Subject to any disclaimer, the term of this patent is extended or adjusted under 35 U.S.C. 154(b) by 194 days.

(21) Appl. No.: 17/009,200

(22) Filed: Sep. 1, 2020

(65) Prior Publication Data

US 2021/0059657 A1    Mar. 4, 2021

Related U.S. Application Data

(60) Provisional application No. 62/894,802, filed on Sep. 1, 2019.

(51) Int. Cl.
| | |
|---|---|
| *A61B 17/02* | (2006.01) |
| *A61M 29/00* | (2006.01) |
| *A61B 46/17* | (2016.01) |
| *A61B 46/23* | (2016.01) |
| *A61B 17/34* | (2006.01) |
| *A61B 17/00* | (2006.01) |

(52) U.S. Cl.
CPC ...... *A61B 17/0206* (2013.01); *A61B 17/0218* (2013.01); *A61B 17/3417* (2013.01); *A61B 46/17* (2016.02); *A61B 46/23* (2016.02); *A61B 2017/00991* (2013.01); *A61B 2017/3433* (2013.01); *A61M 29/00* (2013.01)

(58) Field of Classification Search
CPC ............ A61B 17/0206; A61B 17/0218; A61B 17/3417; A61B 17/3421; A61B 2017/3433; A61B 1/32; A61M 29/00
See application file for complete search history.

(56) References Cited

U.S. PATENT DOCUMENTS

| | | | |
|---|---|---|---|
| 5,104,103 A | 4/1992 | Auchinleck et al. | |
| 5,967,970 A * | 10/1999 | Cowan ............... | A61B 17/3423 600/206 |
| 6,767,153 B1 | 7/2004 | Holbrook | |
| 8,480,576 B2 | 7/2013 | Sandhu | |
| 8,678,009 B2 | 3/2014 | Hagn | |

(Continued)

FOREIGN PATENT DOCUMENTS

CN    209360779 U    9/2019

*Primary Examiner* — Kevin T Truong
*Assistant Examiner* — Tracy L Kamikawa
(74) *Attorney, Agent, or Firm* — Harness, Dickey & Pierce, P.L.C.

(57) ABSTRACT

A surgical system includes a surgical arm including at least a distal segment. The surgical system further includes a drape disposed over the surgical arm such that the surgical arm is at least partially covered by the drape. An instrument connector is coupled to the distal segment of the surgical arm through the drape and includes a stem and a shaft. The shaft is configured to receive a surgical instrument. When the instrument connector is coupled to the surgical arm, the instrument connector secures a portion of the drape against the distal segment of the surgical arm. Other example surgical systems and surgical arms are also disclosed.

7 Claims, 11 Drawing Sheets

(56) References Cited

U.S. PATENT DOCUMENTS

| | | |
|---|---|---|
| 8,834,508 B2 * | 9/2014 | Chin .................. A61B 17/7092 |
| | | 606/191 |
| 8,870,141 B2 | 10/2014 | Abri et al. |
| 9,204,933 B2 | 12/2015 | Reis et al. |
| 9,724,163 B2 | 8/2017 | Orban |
| 9,808,232 B2 * | 11/2017 | Heiman .................. A61B 5/24 |
| 10,299,777 B2 | 5/2019 | Mast et al. |
| 10,357,239 B2 | 7/2019 | Perrow et al. |
| 10,420,622 B2 | 9/2019 | Dachs, II et al. |
| 10,470,830 B2 | 11/2019 | Hill et al. |
| 10,524,866 B2 | 1/2020 | Srinivasan et al. |
| 2006/0270909 A1 | 11/2006 | Davis et al. |
| 2007/0043266 A1 | 2/2007 | Laucirica Gari |
| 2015/0190128 A1 | 7/2015 | Fenn et al. |
| 2017/0007409 A1 | 1/2017 | Mauldin et al. |
| 2017/0296040 A1 | 10/2017 | Haraguchi et al. |
| 2017/0333023 A1 * | 11/2017 | Adams ............... A61B 17/0218 |
| 2018/0116758 A1 | 5/2018 | Schlosser et al. |
| 2018/0206834 A1 | 7/2018 | Villamil et al. |
| 2018/0271513 A1 * | 9/2018 | Perrow ............. A61B 17/0293 |
| 2019/0053826 A1 * | 2/2019 | Bush, Jr. ............... A61B 17/025 |
| 2019/0183590 A1 | 6/2019 | Hladio et al. |
| 2019/0216554 A1 | 7/2019 | Kapadia |
| 2019/0274777 A1 | 9/2019 | Garcia et al. |
| 2020/0405501 A1 * | 12/2020 | Orozco Castillo .. A61B 17/686 |

* cited by examiner

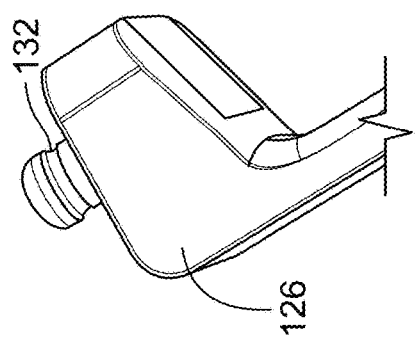
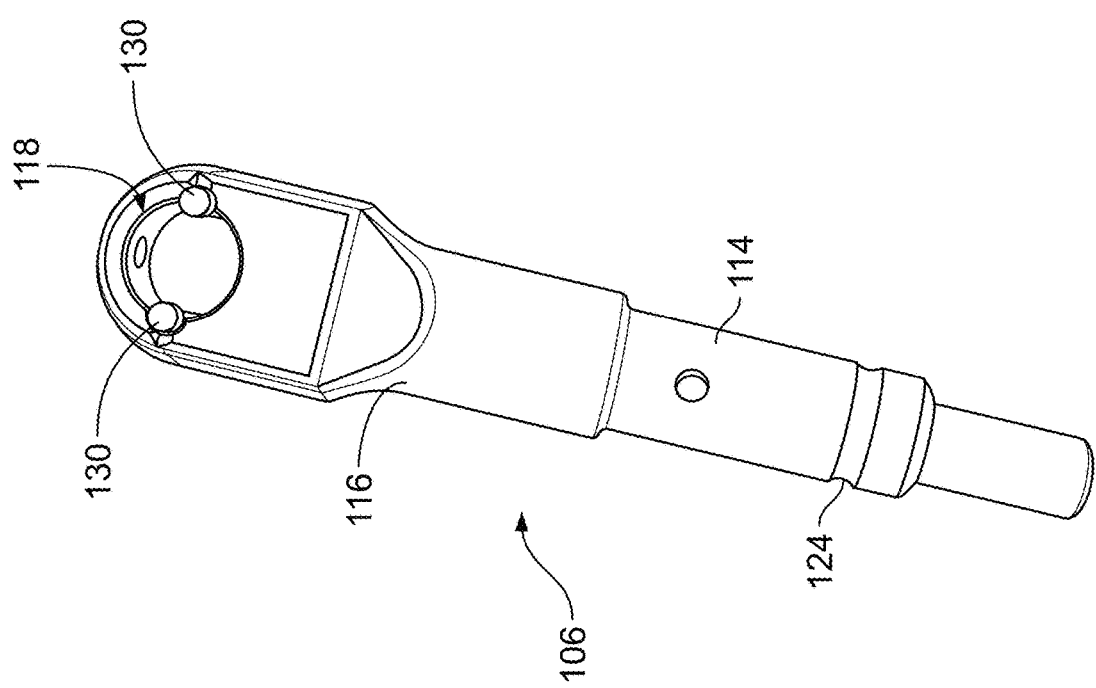

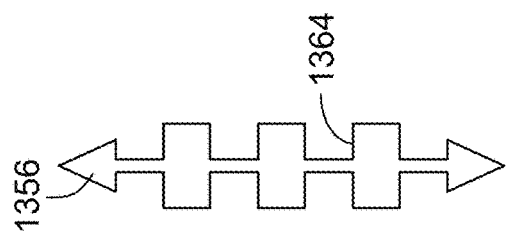
FIG. 15B
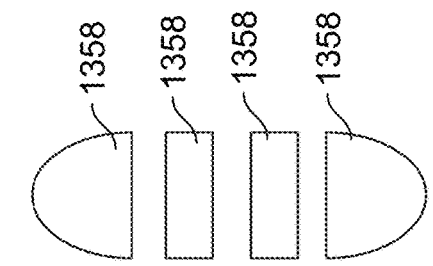
FIG. 16B
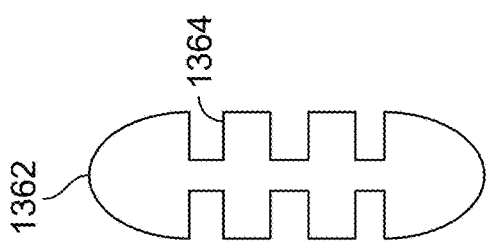
FIG. 15A
FIG. 16A
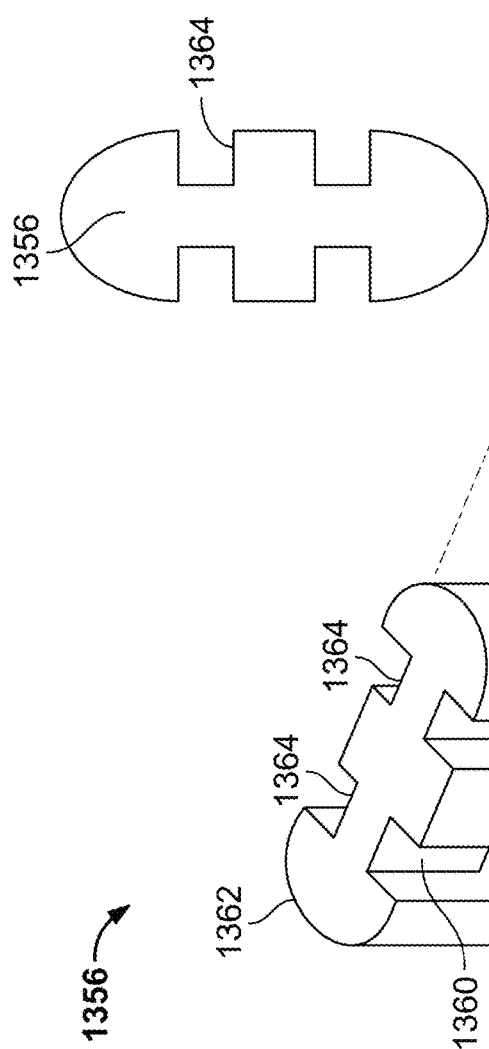
FIG. 14

UNIVERSAL SURGICAL ACCESS SYSTEM

FIELD

The present disclosure relates to surgical systems, and in particular, universal surgical access systems.

BACKGROUND

This section provides background information related to the present disclosure which is not necessarily prior art.

A variety of surgical instruments are often used during surgical procedures. In some of these procedures, one or more instruments, such as a retractor blade, may need to be maintained in a single position for an extended period of time (e.g., for the duration of the surgical procedure). To alleviate the difficulty and/or undesirability of manually holding a position of an instrument for the duration of the surgical procedure, surgical arms can be used to hold the position of the instrument while other aspects of the procedure are performed. Some arms can be adjustable such that a position of the arm can be adjusted before or during the procedure.

SUMMARY

This section provides a general summary of the disclosure, and is not a comprehensive disclosure of its full scope or all of its features.

According to one aspect of the present disclosure, a surgical system includes a surgical arm including at least a distal segment. The surgical system further includes a drape disposed over the surgical arm such that the surgical arm is at least partially covered by the drape. An instrument connector is coupled to the distal segment of the surgical arm through the drape. The instrument connector includes a stem and a shaft. The shaft is configured to receive a surgical instrument. When the instrument connector is coupled to the surgical arm, the instrument connector secures a portion of the drape against the distal segment of the surgical arm.

According to another aspect of the present disclosure, a surgical access system includes a plurality of nesting tubes including an insertion tube of a smallest size, at least one intermediate tube of at least one intermediate size, and a final tube of a largest size. The plurality of tubes are configured for sequential insertion into a patient. The surgical access system further includes a spacer including a plurality of grooves extending along a length of the spacer. The spacer is configured for insertion into the final tube of the plurality of tubes upon removal of the insertion tube and the at least one intermediate tube from the final tube.

According to a further aspect of the present disclosure, a surgical arm includes a plurality of segments including a distal segment, a first intermediate segment, a second intermediate segment, and a proximal segment. A first ball joint is coupled between the distal segment and the first intermediate segment. A telescopic joint is coupled between the first intermediate segment and the second intermediate segment. The telescopic joint permits translation of the first intermediate segment with respect to the second intermediate segment. A second ball joint is coupled between the second intermediate segment and the proximal segment. The distal segment of the surgical arm is configured to receive a surgical instrument and/or an instrument connector.

Further aspects and areas of applicability will become apparent from the description provided herein. It should be understood that various aspects of this disclosure may be implemented individually or in combination with one or more other aspects. It should also be understood that the description and specific examples herein are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7A is a perspective view of the instrument connector of FIG. 5.

FIG. 7B is a perspective view of a portion of a surgical instrument.

FIG. 14 is a perspective view of a spacer of the surgical access system of FIG. 13A.

Figure 13A:
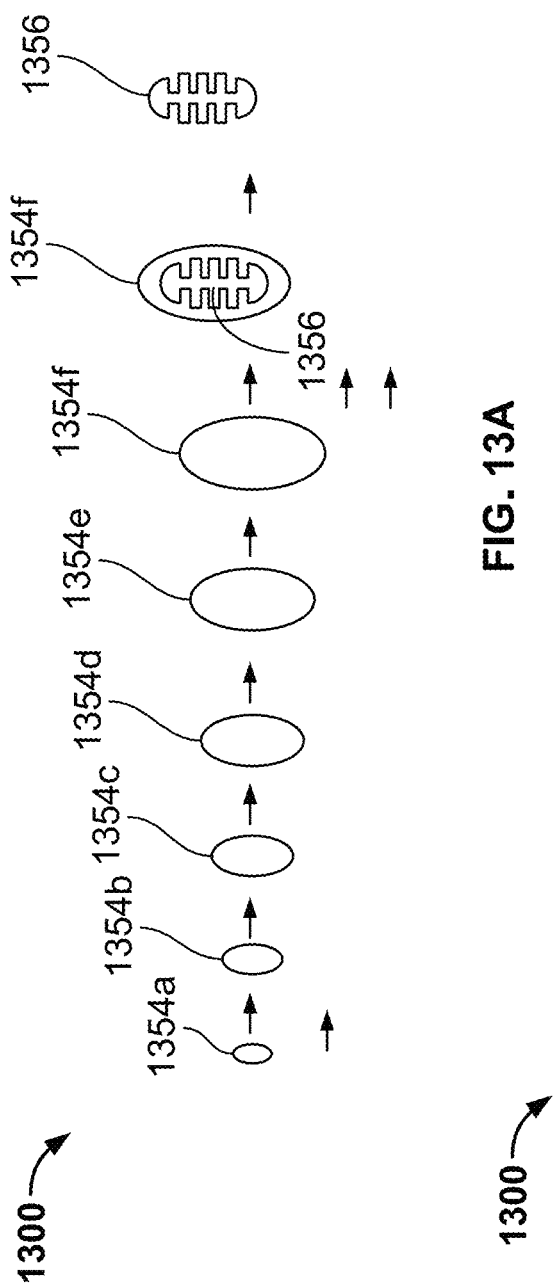
FIG. 13A is a top view of a dilation sequence of a surgical access system.

FIGS. 15A-B are top views of example spacers of the surgical access system of FIG. 13A.

FIG. 16A is a top view of the spacer of FIG. 14.

FIG. 16B is a bottom view of the spacer of FIG. 14.

Figure 17A:
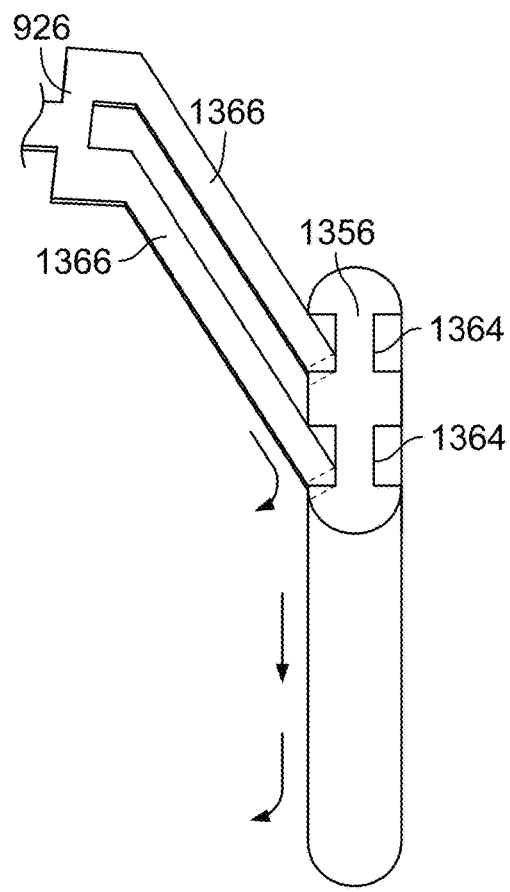
Figure 17B:
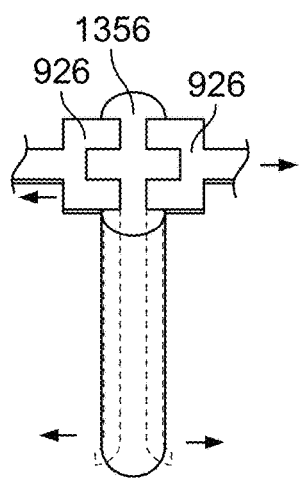

FIGS. 17A-B are perspective views of inserting a retractor blade into the spacer of FIG. 14.

Figure 18:
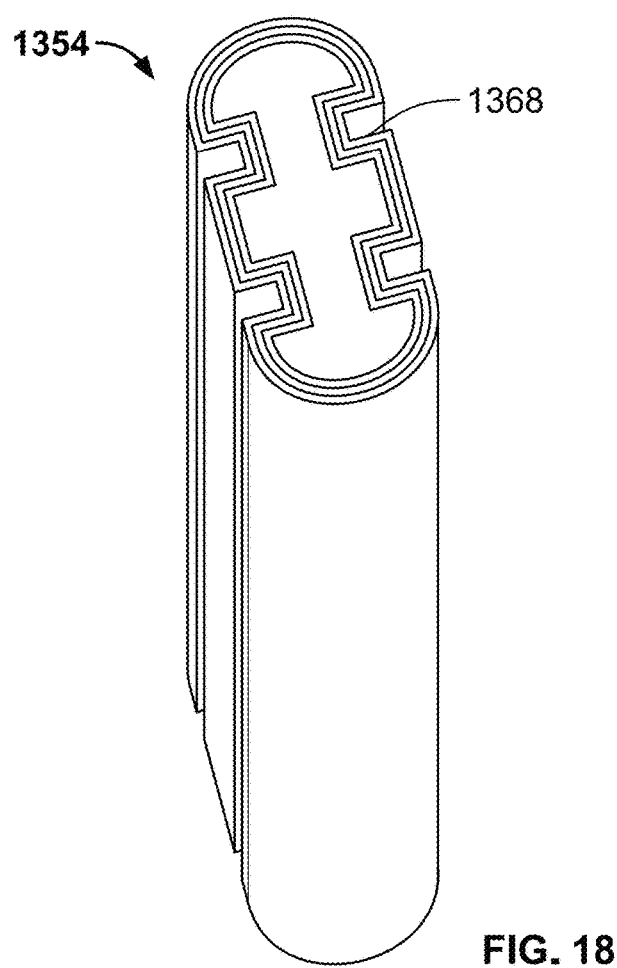

FIG. 18 is a perspective view of an example set of dilation tubes.

Corresponding reference numerals indicate corresponding parts or features throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 1:
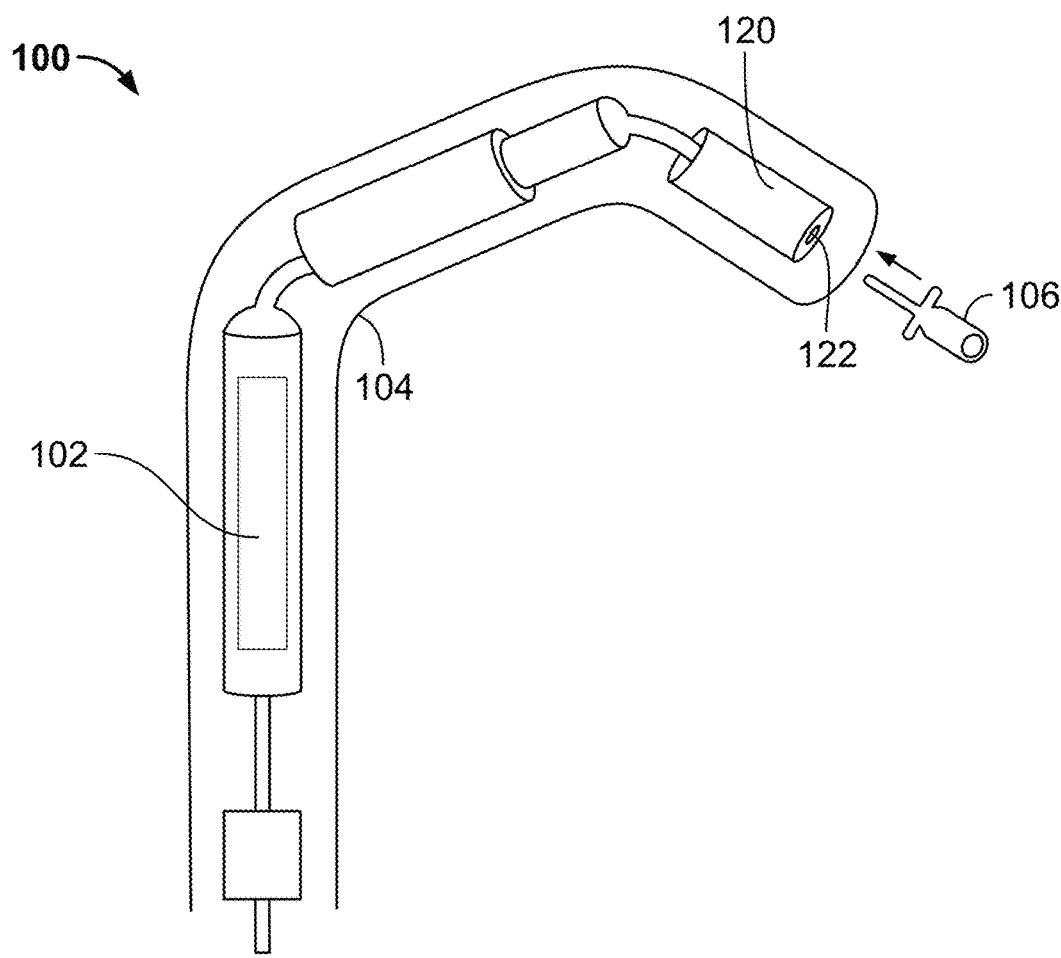
FIG. 1 is a side view of an example surgical system.

A surgical system according to one example embodiment of the present disclosure is illustrated in FIG. 1 and indicated generally by reference number 100. The surgical system 100 includes a surgical arm 102 and a drape 104. The drape 104 is disposed over the surgical arm 102 such that the surgical arm 102 is at least partially covered by the drape 104. The surgical system 100 further includes an instrument connector 106. The instrument connector 106 may be coupled to the surgical arm 102, for example, in connection with surgery to hold a surgical instrument.

Figure 2:
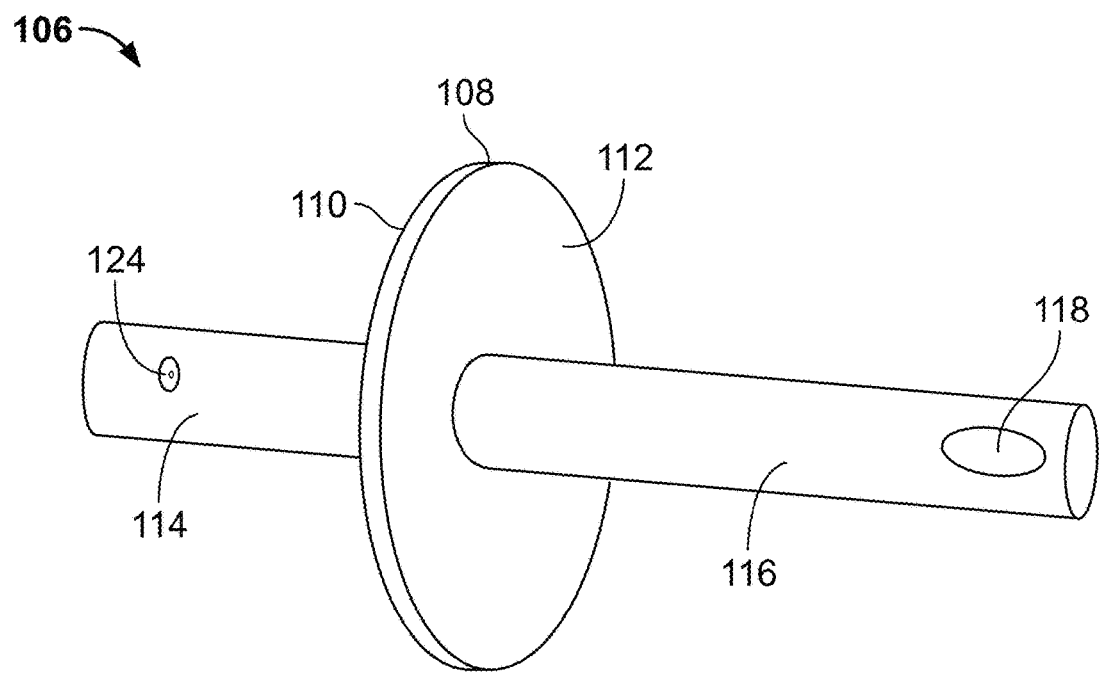
FIG. 2 is a perspective view of an instrument connector included in the surgical system of FIG. 1.

As shown in the embodiment of FIG. 2, the instrument connector 106 includes a plate 108 having a first surface 110 and a second surface 112. In alternate embodiments, the instrument connector 106 does not include plate 108. The instrument connector 106 further includes a stem 114 extending perpendicularly from the first surface 110, and a shaft 116 extending perpendicularly from the second surface 112. In the illustrated embodiment, the stem 114 and the shaft 116 are co-axially aligned (e.g., at a center of plate 108). In other embodiments, the stem 114 and/or the shaft 116 may be offset from the center of the plate 108.

The shaft 116 is configured to receive various surgical instruments (e.g., a retractor blade (such as retractor blade 126 shown in FIG. 3), etc.) via connection 118 (e.g., an opening). Connection 118 is positioned at an end of the shaft 116 (e.g., at the end of shaft 116 away from plate 108). Connection 118 serves as a universal connection point for various surgical instruments, where the surgical instruments may be attached to and removed from the instrument connector 106 without requiring removal of the instrument connector 106 from the surgical arm 102. Connection 118 is described in more detail below.

Figure 4:
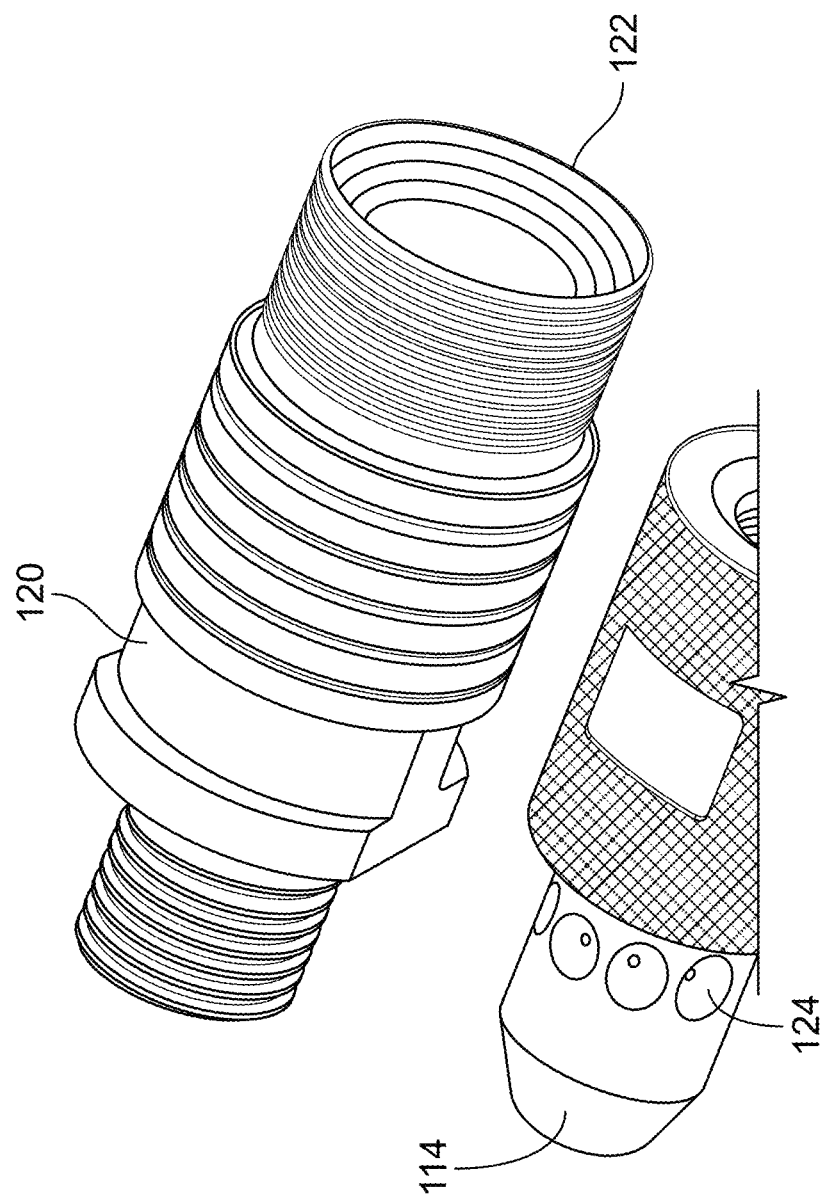
FIG. 4 is a perspective view of another portion of the surgical system of FIG. 1.

The surgical arm 102 includes a distal segment 120. The distal segment 120 of the surgical arm 102 is configured as a cylinder and is generally rigid. In the illustrated embodiment, the instrument connector 106 is coupled to the distal segment 108 of the surgical arm 102 through the drape 104. In some embodiments, the distal segment 108 of the surgical arm 102 includes a socket 122. The socket 122 is configured to receive the stem 114 of the instrument connector 106 and secure and/or lock the instrument connector 106 to the distal segment 120 of the surgical arm 102 while minimizing, or eliminating, rotation of the instrument connector 106. For example, as shown in FIG. 4, in some embodiments, the stem 114 of the instrument connector 106 may include a slot or recess 124 (e.g., a continuous slot, a single dimple or depression, a series of dimples or depressions, etc.) that engages with a protrusion (e.g., a seal) within the socket 122. Additionally, or alternatively, the socket 122 further includes a security lock (not shown) which engages with the instrument connector 106 which must be operated (e.g., by a user) in order to release the instrument connector 106 (e.g., to remove and/or rotate the instrument connector 106).

The drape 104, which is configured to cover the surgical arm 102 (e.g., during surgery), is sterile and comprises a plastic material or other similar material. Covering the surgical arm 102 with the sterile drape 104 avoids the need for sterilization of the entire surgical arm 102 and maintains a sterile environment for surgery. The instrument connector 106 and any surgical instruments for coupling to the instrument connector 106, such as retractor blade 126, are likewise sterile. In the illustrated embodiment, when the instrument connector 106 is coupled to the surgical arm 102 (e.g., after the drape 104 is positioned over the surgical arm 102), the first surface 110 of the plate 108 secures a portion of the drape 104 against the distal segment 120 of the surgical arm 102. By securing the drape 104 to the surgical arm 102, the sterile environment is maintained and potential for breach of the sterile environment (e.g., caused by movement of the drape) is reduced. That is, the drape 104 covers potentially non-sterilized equipment, such as the surgical arm 102, and prevents inadvertent exposure of such equipment.

Figure 3:
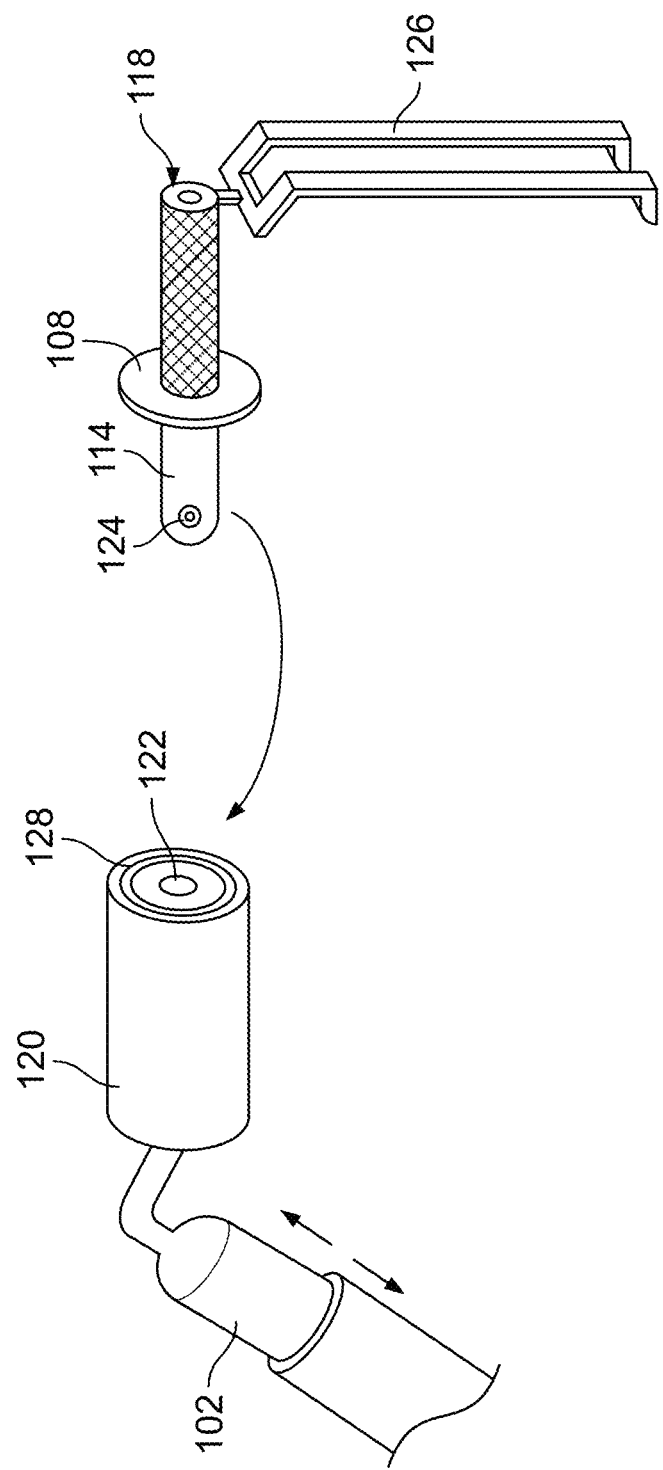
FIG. 3 is a perspective view of a portion of the surgical system of FIG. 1.

In connection therewith, in some embodiments, the distal segment 120 of the surgical arm 102 includes a seal 128 to further ensure the drape 104 is retained against the distal segment 120 of the surgical arm 102. As shown in FIG. 3, the seal 128 is annular and is positioned at the distal end of the distal segment 120 between an outer edge of the distal segment 120 and the socket 122. For example, the distal end of the distal segment 120 further includes an annular channel or recess in which the seal 128 is positioned (i.e., the seal 128 is seated within the annual channel or recess). Seal 128 may comprise a rubber material, or other similar material. In other embodiments, the seal 128 may be positioned at a different location of distal segment 120, such as within the socket 122 (e.g., within an annular channel or recess included within the socket 122).

Figure 5:
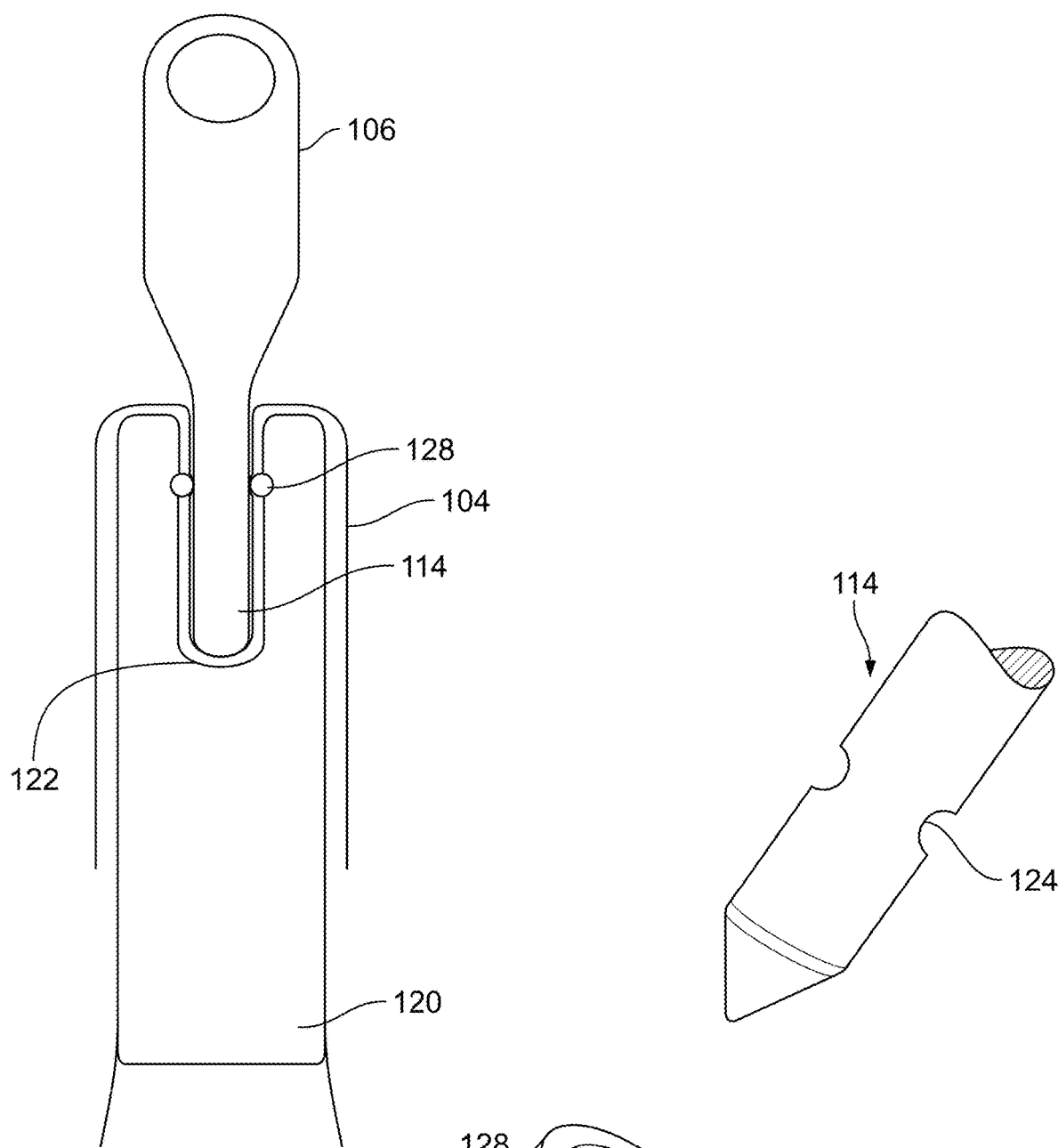
FIG. 5 is a side view of another example of an instrument connector included in the surgical system of FIG. 1.

In an alternate embodiment, the instrument connector 106 does not include plate 108, as shown in FIG. 5. Without plate 108, there is no compression of the drape 104 against the distal end of the distal segment 120 by plate 108. Rather, in the alternate embodiment, the seal 128 is positioned inside of socket 122 instead of being positioned on the distal end of the distal segment 120. Then, when stem 114 is inserted into socket 122, sealing pressure is created between seal 128 and stem 114 to ensure drape 104 is retained against the distal segment 120 of the surgical arm 102. As shown in the illustrated embodiment, the seal 128 is included towards the distal end of the socket 122. However, the seal may be positioned at other depths of the socket 122 without departing from the scope of the present disclosure.

In this embodiment, the slot 124 engages with the seal 128 such that seal 128 is seated on, or within, the slot 124. When the instrument connector 106 is coupled to the surgical arm 102 (e.g., after the drape 104 is positioned over the surgical arm 102), the stem 114 guides the drape 104 into the socket 122. When the slot 124 engages with the seal 128 (with the drape 104 between the slot 124 and the seal 128), a portion of the drape 104 is secured against the socket 122 of the distal segment 120 of the surgical arm 102 and the seal 128 is seated on the slot 124. By securing the drape 104 to the surgical arm 102, a sterile environment is maintained and potential for breach of the sterile environment (e.g., caused by movement of the drape) is reduced. That is, the drape 104 covers potentially non-sterilized equipment, such as the surgical arm 102, and prevents inadvertent exposure of such equipment.

Figure 6:
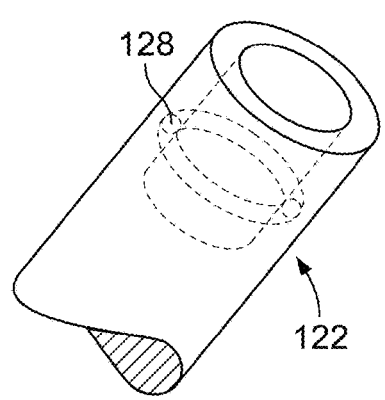
FIG. 6 is a perspective view of another portion of the surgical system of FIG. 1.

In some embodiments, the instrument connector 106 (with or without plate 108) is configured to pierce the drape 104 as the instrument connector 106 is coupled to the surgical arm 102. To pierce the drape 104, the stem 114 of the instrument connector 106, in some embodiments, as shown in FIG. 6, is tapered at an end (e.g., the end of the stem 114 away from plate 108). For example, as the instrument connector 106 is inserted into the socket 122 of the distal segment 120 of the surgical arm 102, the stem 114 pierces the drape 104 and, in doing so, breaches the boundary of the sterile environment established by the drape 104. However, as the boundary is breached (i.e., as the drape 104 is pierced), the instrument connector 106 simultaneously seals the drape 104 to the surgical arm 102 (e.g., at seal 128, by plate 108 or slot 124). The simultaneous piercing and sealing action that occurs as the instrument connector 106 is inserted into the distal segment 120 of the surgical arm 102 relocates the boundary of the sterile environment from the outer surface of the drape 104 to the connection point between the drape 104 and the instrument connector 106. As such, even though the drape 104 is pierced by the instrument connector 106, sterility is not compromised and the sterile environment is maintained.

In further embodiments, the drape 104 may include perforations and/or scoring to enable piercing of the drape 104. In other embodiments, instead of the drape 104 being pierced, the drape 104 may be inserted into the socket 122 of the distal segment 120 (e.g., without piercing and/or breaking drape 104) when the instrument connector 106 is coupled to the distal segment 120 (i.e., both a portion of the drape 104 and the stem 114 of the instrument connector 106 are inserted into the socket 122 without puncturing the drape 104). In some embodiments, the stem 114 may be tapered without piercing the drape 104.

By sealing the sterile drape 104 to the surgical arm 102 with the instrument connector 106, tape or other means for fixing the drape 104 to the surgical equipment (e.g., a surgical arm and/or an instrument connector, etc.) is eliminated. Further, the time required to secure a drape to a surgical arm and/or instrument connector is reduced, as tape does not have to be applied. And, in some embodiments, the connection created between the surgical arm 102 and the instrument connector 106 may more securely retain the drape 104 than tape or other conventional means of securing a sterile drape during surgery (e.g., elastic portions of sterile drapes). Similarly, the time required to sterilize the equipment prior to surgical use may be reduced as the sterilization of the surgical arm 102 is achieved using the sterile drape 104 (i.e., it is not required for the surgical arm 102 itself to be sterilized before using the arm 102). Further, when the instrument connector 106 is coupled to the socket 122 of the surgical arm 102, the seal created by the instrument connector 106 between the surgical arm 102 and the drape 104 avoids contact between sterilized and non-sterilized components. This allows surgical instruments (e.g., retractor blades 126, etc.) attached to the instrument connector 106 to be changed as many times as needed, without breaking the sterilized field.

As indicated above, the instrument connector 106, when coupled to the surgical arm 102 through the drape 104, permits attachment of a surgical instrument, such as retractor blade 126, to the surgical arm 102. Referring again to FIG. 3, retractor blade 126 includes a plurality of fork-like prongs or tines. In some embodiments, the prongs of the retractor blade 126 are curved to facilitate grip of soft tissue, etc. However, other suitable retractors of other configurations and/or other surgical instruments may be interchangeably used in connection with surgical system 100. Surgical instruments may be attached to and removed from instrument connector 106 while instrument connector 106 is coupled to the surgical arm 102 in a manner that maintains sterility (e.g., without removing the instrument connector 106 from the surgical arm 102). In this way, instrument connector 106 permits quick attachment of different sterile tools for use during surgery, which may be switched several times without impairing the sterility of the environment. These different surgical retractor blades or tools can be connected through connection 118 while maintaining the sterile environment. Alternatively, surgical instruments may be directly coupled to the surgical arm 102 (e.g., without instrument connector 106).

With reference to FIGS. 7A-7B, connection 118 includes a plurality (e.g., two, three, etc.) of retracting pins 130. When a surgical instrument (e.g., retractor blade 126) is inserted into connection 118, the retracting pins 130 initially retract and then expand to press into a slot 132 of the surgical instrument and secure the instrument to the instrument connector 106.

Figure 8:
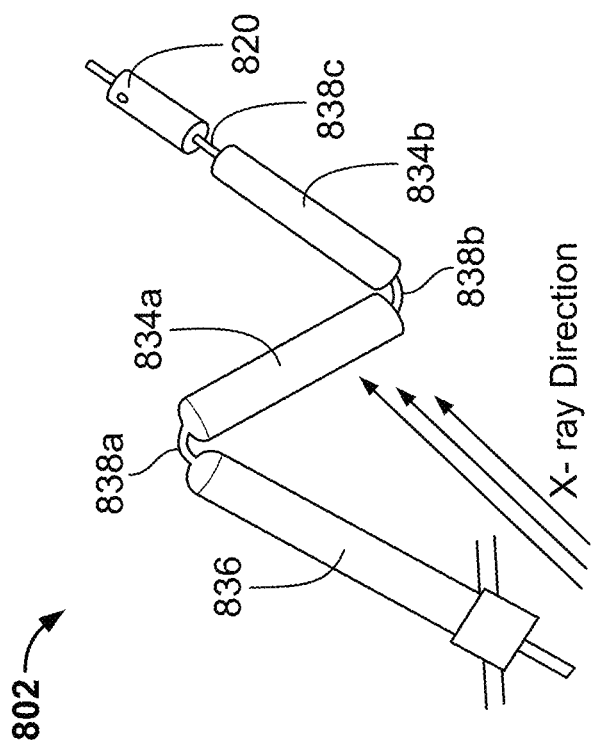
FIG. 8 is a side view of an example surgical arm.

FIGS. 8-12 illustrate embodiments of surgical arms, including surgical arms similar to surgical arm 102, which may be included in surgical system 100. As shown in FIG. 8, surgical arm 802 is an articulated surgical arm that includes a plurality of segments, including a distal segment 820 (e.g., similar to distal segment 120), one or more intermediate segments 834, and a proximal segment 836. In the illustrated embodiment, the surgical arm 802 includes two intermediate segments 834 (e.g., a first intermediate segment 834*a* and a second intermediate segment 834*b*). However, in other embodiments, a greater or fewer number of intermediate segments 834 may be included in surgical arm 802. The segments are generally cylindrical and are formed of a rigid material. The articulated surgical arm 802 further includes a plurality of joints 838, where each joint is coupled between an adjacent pair of segments. In particular, a first joint 838a is positioned between the proximal segment 836 and the first intermediate segment 834a. A second joint 838b is positioned between the first intermediate segment 834a and the second intermediate segment 834b. A third joint 838c is positioned between the second intermediate segment 834b and the distal segment 820. In the illustrated embodiment, each of the joints (i.e., joints 838a, 838b, 838c) are configured as ball joints. The ball joints permit rotational movement (e.g., along two planes at the same time) and restrict translation (e.g., in any direction).

The joints 838a, 838b, 838c of surgical arm 802 may be maintained in either a locked position or an unlocked position through a locking mechanism (e.g., a pneumatic and/or electromagnetic locking mechanism) which enables selective mobility of the segments 820, 834a, 834b, 836 of the surgical arm 802 via the joints 838a-c. In the locked position, the segments 820, 834a, 834b, 836 are fixed in a stable position, such that the surgical arm 802 maintains the stable, fixed position during surgery (e.g., during submission of the surgical arm 802 to soft tissue pressure, etc.). In the unlocked position, each of the segments 820, 834a, 834b, 836 of the surgical arm 802 are freely moveable via the joints 838a-c within a predetermined range determined based on the selected ball joints. The size of the segments (i.e., segments 820, 834a, 834b, and 836) and joints (i.e., joints 838a-c) may vary depending on the forces required to maintain the joints in the locked position while withstanding surgical pressures (e.g., soft tissue pressures).

Figure 9:
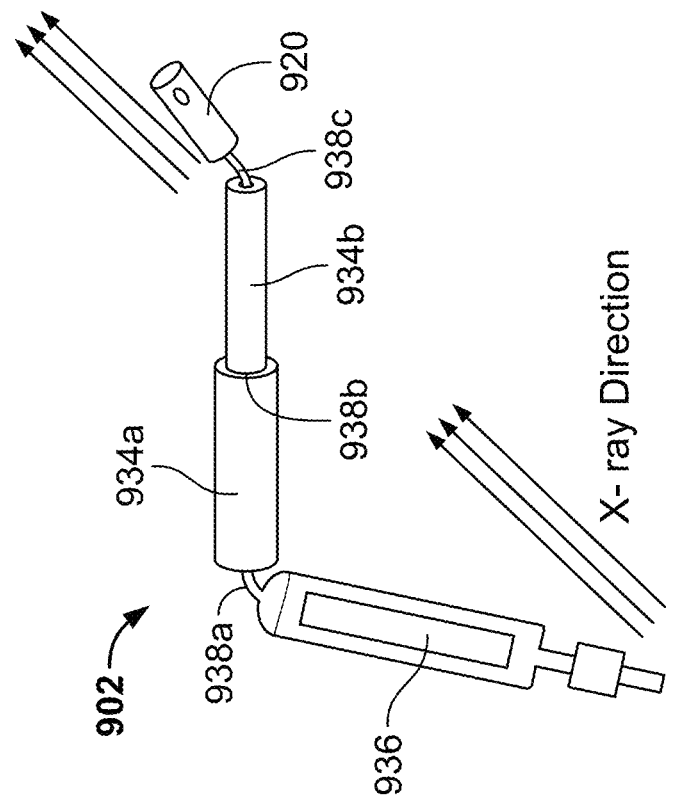
FIG. 9 is a side view of another example surgical arm.

An alternate, articulated surgical arm, that includes a different configuration of joints than surgical arm 802, is illustrated in FIG. 9 and indicated generally by reference number 902. Similar to surgical arm 802, surgical arm 902 includes a plurality of segments, including a distal segment 920, one or more intermediate segments 934, and a proximal segment 936. In the illustrated embodiment, the surgical arm 902 includes two intermediate segments 934 (e.g., a first intermediate segment 934a and a second intermediate segment 934b). However, in other embodiments, a greater or fewer number of intermediate segments 934 may be included in surgical arm 902 (e.g., three intermediate segments, as shown in FIG. 6). The segments are generally cylindrical and are formed of a rigid material. The articulated surgical arm 902 further includes a plurality of joints 938, where a joint is coupled between each adjacent pair of segments. A first joint 938a is positioned between the proximal segment 936 and the first intermediate segment 934a. A second joint 938b is positioned between the first intermediate segment 934a and the second intermediate segment 934b. A third joint 938c is positioned between the second intermediate segment 934b and the distal segment 920. In contrast to surgical arm 802, the joints 938 of surgical arm 902 include a combination of ball joints as well as telescopic joints. While the ball joints restrict translation, telescopic joints permit translation of the segments coupled thereto. In the illustrated embodiment, joints 938a and 938c are configured as ball joints and joint 938b is configured as a telescopic joint. The telescopic joint 938b enables translation of the first intermediate segment 934a with respect to the second intermediate segment 934b (e.g., when telescopic joint 938b is in an unlocked position). In some embodiments, joints 938 are independent of any actuator, such that the segments coupled by the joints 938 are configured for manual manipulation and/or positioning.

The joints 938a-c of surgical arm 902 may be maintained in either a locked position or an unlocked position through a locking mechanism (e.g., a pneumatic and/or electromagnetic locking mechanism) which enables selective mobility of the segments 920, 934a, 934b, 936 of the surgical arm 902 via the joints 938a-c. In the locked position, the segments 920, 934a, 934b, 936 are fixed in a stable position, such that the surgical arm 902 maintains the stable position during surgery (e.g., during submission of the surgical arm 902 to soft tissue pressure, etc.). In the unlocked position, each of the segments 920, 934a, 934b, 936 of the surgical arm 902 are freely moveable via the joints 938a-c within a predetermined range determined based on the selected ball and/or telescopic joints. For example, in the unlocked position, first intermediate segment 934a is able to slide and/or translate with respect to second intermediate segment 934b within a predetermined distance defined by the selected telescopic joint 938b positioned between such segments. The size of the segments (i.e., segments 920, 934a, 934b, and 936) and joints (i.e., joints 938a-c) may vary depending on the forces required to maintain the joints in the locked position while withstanding surgical pressures (e.g., soft tissue pressures).

Comparing FIGS. 8 and 9, the configuration of joints of surgical arm 902 (i.e., a configuration including a combination of ball joints and telescopic joints) may provide certain advantages over a configuration that only includes ball joints (e.g., the configuration of joints of surgical arm 802). In particular, when surgical arms are used in connection with various scans or imaging, such as intraoperative fluoroscopic x-ray imaging, a surgical arm including a combination of ball joints and telescopic joints (e.g., as opposed to only ball joints) may be more conveniently manipulated and/or positioned in a manner that ensures the surgical arm does not interfere with the scan (e.g., does not obstruct the path of the x-rays). Moreover, such a configuration of joints enables a less bulky surgical arm as one or more segments of the surgical arm is able to slide within another segment (e.g., at least partially retract within an adjacent segment, as shown in FIG. 8, etc.). In this way, the combination of ball joints and telescopic joints improves the convenience and flexibility of articulated surgical arms and enables use of such surgical arms in a wide variety of surgical procedures.

Figure 10:
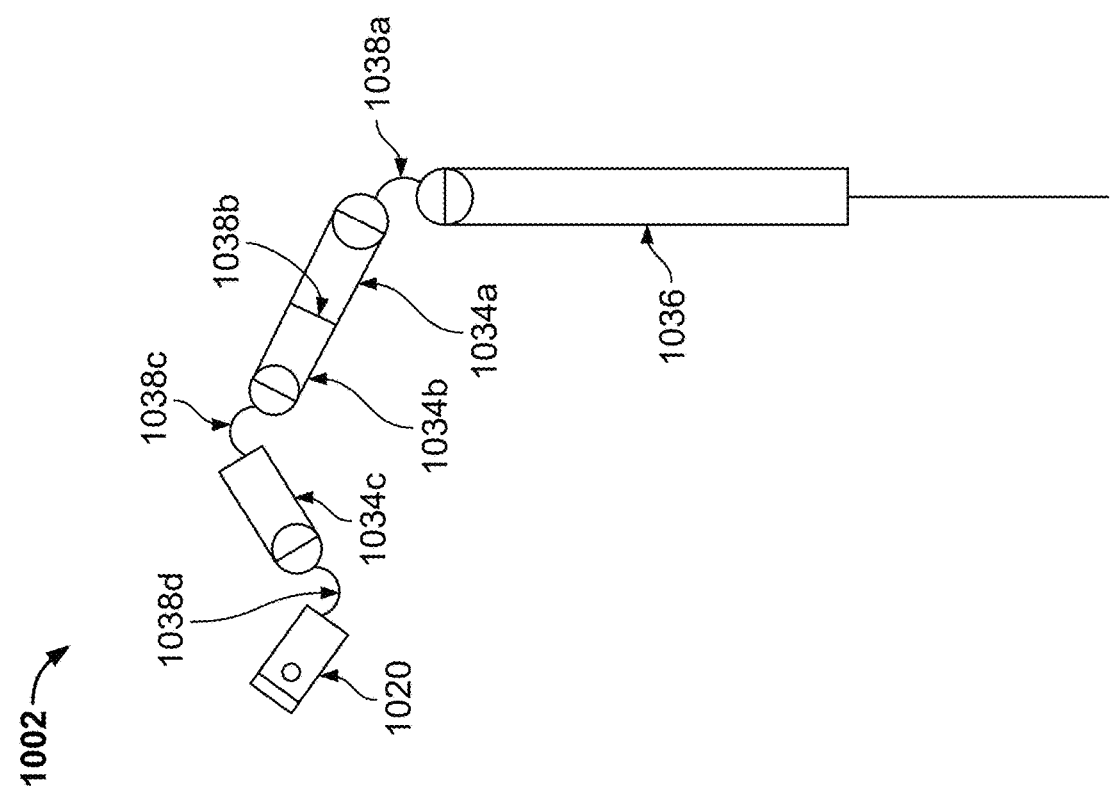
FIG. 10 is a side view of yet another example surgical arm.

FIG. 10 illustrates a surgical arm 1002 that includes both ball joints and a telescopic joint, similar to surgical arm 902. However, surgical arm 1002 includes an additional intermediate segment. In particular, surgical arm 1002 includes a distal segment 1020, a first intermediate segment 1034a, a second intermediate segment 1034b, a third intermediate segment 1034c, and a proximal segment 1036. The surgical arm 1002 further includes a plurality of joints 1038, where a joint is coupled between each adjacent pair of segments. A first joint 1038a is positioned between the proximal segment 1036 and the first intermediate segment 1034a. A second joint 1038b is positioned between the first intermediate segment 1034a and the second intermediate segment 1034b. A third joint 1038c is positioned between the second intermediate segment 1034b and the third intermediate segment 1034c. A fourth joint 1038d is positioned between the third intermediate segment 1034c and the distal segment 1020. In the illustrated embodiment, the second joint 1038b is a telescopic joint and the other joints (e.g., joint 1038a, joint 1038c, and joint 1038d) are configured as ball joints. While the second joint 1038b of surgical arm 1002 is depicted as a telescopic joint, any other joint(s) (e.g., joint 1038a, joint 1038c and/or joint 1038d) may additionally or alternatively be configured as a telescopic joint in other embodiments.

Figure 11:
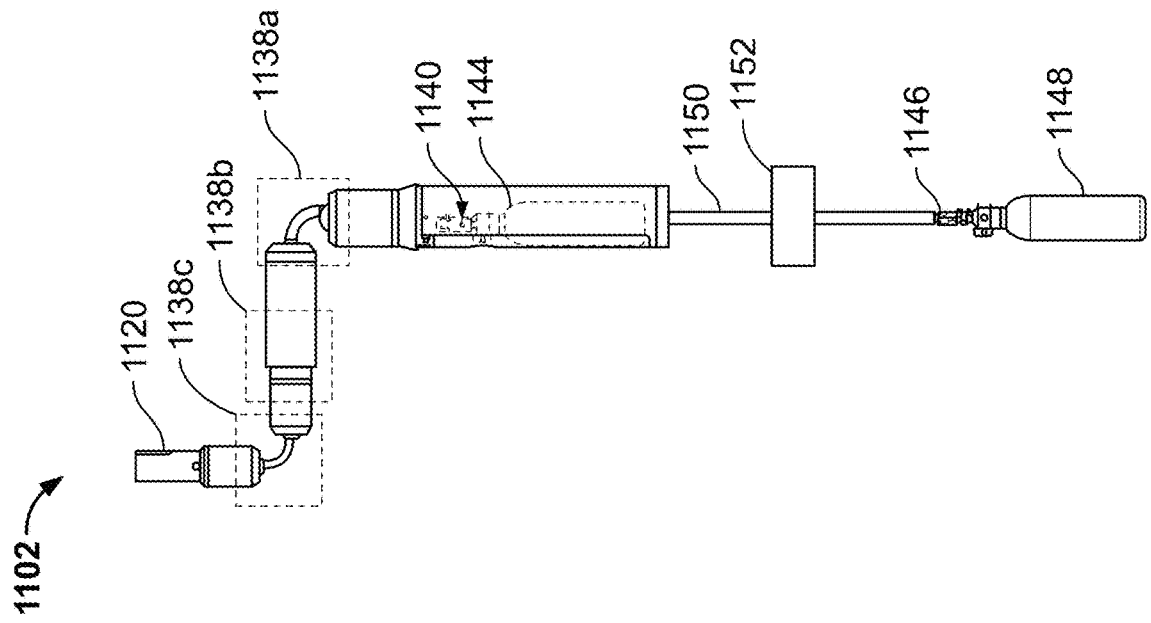
FIG. 11 is a side view of another example surgical arm.
Figure 12:
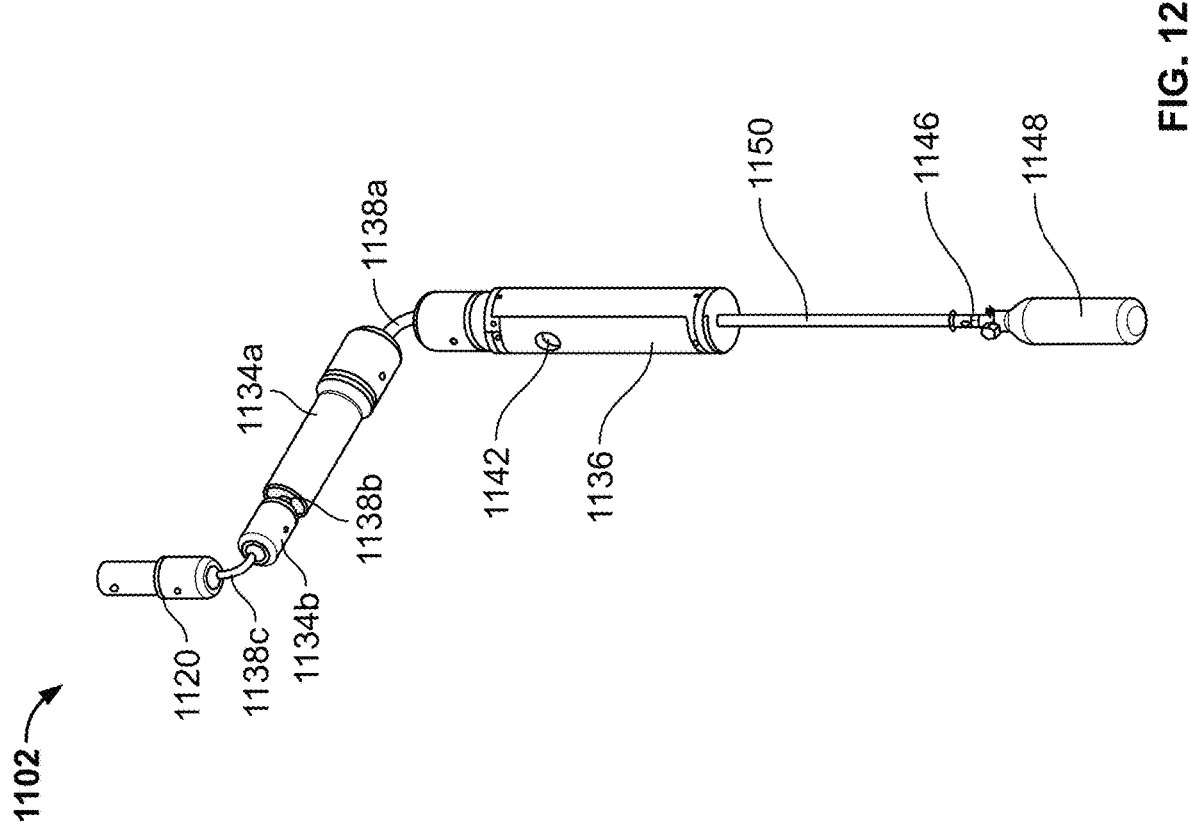
FIG. 12 is a perspective view of the surgical arm of FIG. 11.

Another embodiment of a surgical arm which may be included in surgical systems (e.g., surgical system 100) is shown in FIGS. 11-12 and indicated by reference number 1102. Similar to the surgical arms described above, surgical arm 1102 includes a plurality of segments (i.e., segments 1120, 1134a-b, 1136) and a plurality of joints (e.g., joints 1138a-c). Similar to surgical arms 902 and 1002, the joints 1138a-c of surgical arm 1102 are configured as a combination of ball joints (e.g., 1138a, 1138c) and a telescopic joint (e.g., joint 1138b). Mobility at the joints (e.g., ball joints and/or telescopic joints) may be controlled through a pneumatic and/or electromagnetic locking mechanism 1140. Locking mechanism 1140 allows a complete lock of the joints 1138 when the surgical arm 1102 is in the locked position, and free movement of the segments 1120, 1134a-b, 1136 of the surgical arm 1102 within a predetermined range (e.g., as permitted based upon the selected joints 1138, etc.) when the surgical arm 1102 is in the unlocked position. The locking mechanism 1140 further includes a control 1142 such as a button, a switch, etc. to toggle between the locked position and the unlocked position (e.g., to permit locking and/or unlocking of the joints 1138a-c of the surgical arm 1102). Alternatively, the control 1142 may be separate from the surgical arm 1102, such as a remote and/or a foot pedal. In other embodiments, control 1142 may enable locking and/or unlocking of the joints 1138a-c of the surgical arm 1102 through voice control.

In some embodiments, the locking mechanism 1140 includes pneumatic control. In such embodiments, an internal supply 1144 of gas (e.g., a container of gas, such as a cylinder or bottle, etc.) may be positioned within the proximal segment 1136 of the surgical arm 1102. For example, the proximal segment 1136 may include an internal, integrated slot for receiving the internal supply 1144. Alternatively, gas may be supplied for pneumatic control of the locking mechanism 1140 via an external connection 1146 (e.g., a threaded connection at a hose). With the external connection 1146, an external supply 1148 of gas (e.g., as provided in an operating room) may be connected to the locking mechanism 1140.

In some embodiments, the locking mechanism 1140 utilizes electromagnetics to provide the locking and unlocking of the surgical arm 1102. In these embodiments, the internal supply 1144 is a power supply such as a battery, positioned within the proximal segment 1136 of the surgical arm 1102. Alternatively, power may be supplied for electromagnetic control of the locking mechanism 1140 via external connection 1146 (e.g., configured as a power cord) which is attached to external supply 1148 (e.g., an external power supply provided in an operating room, etc.). When the gas and/or power for locking mechanism 1140 is supplied internally via internal supply 1144, a surgical system (e.g., surgical system 100) acquires complete autonomous functionality without the need of connecting to external air or power supply (such as external supply 1148).

Surgical arm 1102 further includes a base segment 1150 that is coupled to proximal segment 1136. Base segment 1150 is configured as cylinder or tube, which may be of a smaller diameter that proximal segment 1136. Base segment 1150 enables surgical arm 1102 to be fixed to a stable structure 1152, such as a table of an operating room, the floor of the operating room, or ceiling of the operating room.

To enable use of surgical instruments (e.g., retractor blade 126 as held by surgical arm 102) for surgery, an access channel must be created to permit entry of such surgical instruments into a patient. FIGS. 13-18 illustrate a percutaneous access system 1300 for creating such an access channel. The access channel created by access system 1300 may be maintained (e.g., held open) by surgical system 100. For example, surgical arm 102 of surgical system 100 may position retractor blade 126 (which is coupled to surgical arm 102 via instrument connector 106) in a manner that maintains the access channel. Retractor blade 126 may be inserted into the access channel through the percutaneous access system 1300, thus enabling minimally invasive access for surgery.

Figure 13B:
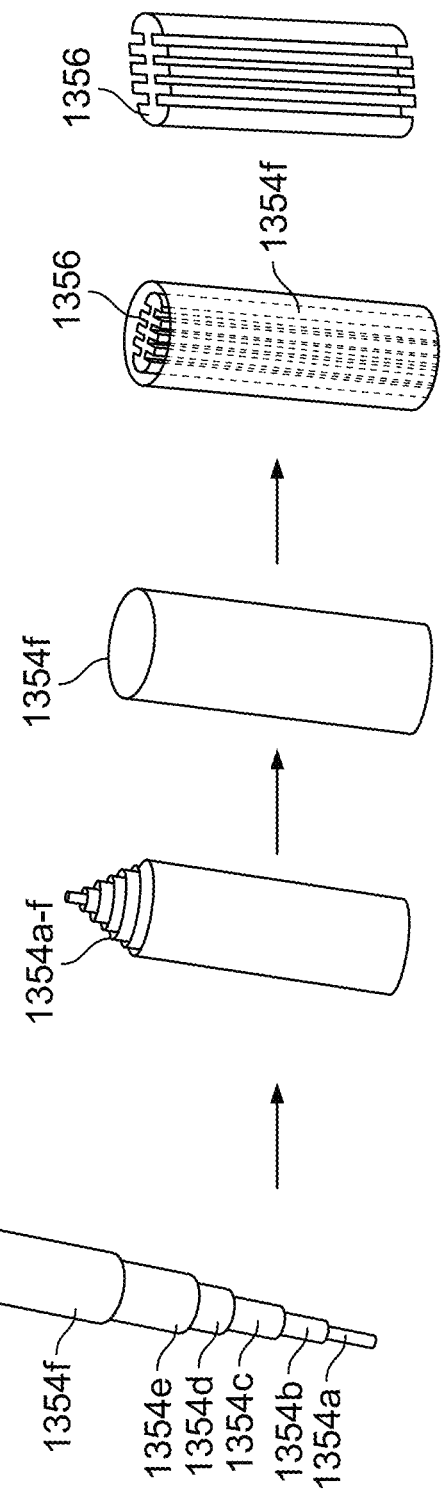
FIG. 13B is a side view of the dilation sequence of the surgical access system of FIG. 13A.

With reference to FIGS. 13A-B, the percutaneous access system 1300 includes a plurality of nesting tubes 1354 and a spacer 1356. The plurality of tubes 1354 includes an insertion tube 1354a of a smallest size, multiple intermediate tubes 1354b-e of graduated intermediate sizes, and a final tube 1354f of a largest size. The plurality of tubes 1354 are configured for sequential insertion into a patient. For example, in use (e.g., during surgery), insertion tube 1354a is initially inserted at a location where an access channel is desired. Subsequently, intermediate tube 1354b is inserted at the location, around insertion tube 1354a (i.e., such that insertion tube 1354a is nested within intermediate tube 1354b). Intermediate tube 1354b has a diameter that is larger than a diameter of insertion tube 1354a to enable insertion of intermediate tube 1354b at the same location without requiring removal of insertion tube 1354a. Because the diameter of intermediate tube 1354b is slightly larger than insertion tube 1354a, insertion of the intermediate tube 1354b causes dilation of the surrounding soft tissue.

Subsequent intermediate tubes 1354c-e are sequentially inserted around the prior inserted tube (e.g., intermediate tube 1354c is inserted around intermediate tube 1354b, intermediate tube 1354d around intermediate tube 1354c, etc.). As shown in FIGS. 13A-B, each subsequent intermediate tube includes a diameter that is of a larger, graduated size than the prior intermediate tube, which causes further dilation of the surrounding soft tissue. While four intermediate tubes 1354b-e are shown in the illustrated embodiment, other embodiments may include a greater or fewer number of intermediate insertion tubes (e.g., depending on the desired dilation, size of the access channel, size of surgical instruments, etc.).

After insertion of the insertion tube 1354a and the intermediate tubes 1354b-e, a final tube 1354f is inserted around intermediate tube 1354e. Final tube 1354f is the largest of the plurality of tubes (e.g., has a diameter that is larger than a diameter of intermediate tube 1354e) and generally corresponds to a desired size of the access channel (e.g., large enough to allow insertion of a surgical instrument therethrough). In the illustrated embodiment, the plurality of tubes 1354 include a cross-section of an oval. However, in other embodiments, the plurality of tubes 1354 may include other cross-sectional shapes, such as circular, rectangular, etc. The plurality of tubes 1354 are generally of a uniform length, however, in some embodiments, the plurality of tubes 1354 may be of different lengths.

The percutaneous access system 1300 also includes spacer 1356 which is configured for insertion into final tube 1354f. For example, spacer 1356 has an outer diameter that is smaller than an inner diameter of final tube 1354f (e.g., equal to the diameter of intermediate tube 1354e, etc.). Spacer 1356 is able to be inserted into final tube 1354f upon removal of insertion tube 1354a and intermediate tubes 1354b-e.

As best shown in FIG. 14, spacer 1356 includes a plurality of extensions 1358 which extend along a length L of the spacer 1356. In the illustrated embodiment, spacer 1356 includes three extensions 1358. In other embodiments, a greater or lesser number of extensions 1358 may be included, for example, depending on the retractor blade selected for maintaining the access channel (e.g., depending on a number of prongs included on the retractor blade). Spacer 1356 further includes a header 1360 positioned between the extensions 1358. The header 1360 is narrower than the extensions 1358, such that outer edge 1362 at the top of the spacer 1356 includes grooves 1364. Grooves 1364 are defined by the header 1360 and the extensions 1358, such that the number of grooves 1364 is dependent on the number of extensions 1358. In the illustrated embodiment, two grooves 1364 are depicted on each side of the spacer 1356. In other embodiments, a greater or lesser number of grooves 1364 may be included on the spacer 1356 (e.g., depending on the selected retractor blade, etc.). A spacer 1356 having a greater number of grooves 1364 (e.g., four grooves on each side of spacer 1356) is depicted in FIG. 11B.

The header 1360 extends along only a portion of the length of the spacer 1356, such that a cross section taken at a top portion of the spacer 1356 (e.g., including the header) is different than a cross section of a bottom portion of the spacer 1356. Such a configuration enables the insertion of curved retractor blades (e.g., in an arcuate motion, etc.). As shown in FIG. 14, the spacer 1356 is generally oval in shape, apart from the grooves 1364. In alternate embodiments, the spacer 1356 may be of other geometries, such as generally circular (as shown in FIG. 11A), more elongated (as shown in FIG. 11B), etc. The shape of the spacer 1356 generally corresponds with the shape of the plurality of tubes 1354.

A top view of the spacer 1356 is illustrated in FIG. 16A and a bottom view of the spacer 1356 is illustrated in FIG. 16B. As shown in FIG. 16A, outer edge 1362 includes multiple grooves 1364 which are sized and spaced to receive prongs of a retractor blade (e.g., retractor blade 126). As shown in FIG. 16, header 1360 does not extend to the bottom of the spacer 1356. In this way, when a retractor blade (e.g., retractor blade 126) is inserted through the grooves 1364 of spacer 1356, the retractor blade may be inserted at an angle, such as to accommodate retractor blades including curved prongs or teeth.

With continued reference to FIGS. 13A-B, the bottom portion of spacer 1356 is inserted into final tube 1354*f* of access system 1300 (e.g., such that extensions 1358 of spacer 1356 are inserted initially, such that header 1360 is not inserted, etc.). After spacer 1356 is inserted within final tube 1354*f*, the final tube 1354*f* is subsequently removed, while the spacer 1356 remains inserted. Spacer 1356 retains the dilation of the soft tissue and enables insertion of retractor blades having multiple prongs via grooves 1364 of spacer 1356. FIGS. 13A-B depict insertion of retractor blades 926 through spacer 1356. As illustrated, retractor blade 926 has a number of prongs 1366 corresponding to the number of grooves 1364 included in spacer 1356. For example, in the illustrated embodiment, each side of the spacer 1356 includes two grooves 1364, such that two retractor blades 926, which each include two prongs 1366, may be inserted through the spacer 1356. Retractor blade 926 is inserted through the spacer 1356 as indicated by arrows in FIG. 13A. Spacer 1356 enables insertion of retractor blades 126 that include prongs 1366 having a curved portion by including header 1360 at an upper position of spacer 1356. Retractor blades 126 with prongs 1366 having a curved portion (e.g., a lip or tooth shaped ending) are able to hold underneath the soft tissue, avoiding soft tissue creep and improving significantly a firm final position. Then, after insertion, retractor blades 926 are retracted, as indicated by arrows in FIG. 13B, to cause further dilation of the surrounding soft tissue, as desired. In this way, retractor blades 926 may separate from spacer 1356 and allow removal of the spacer 1356. Removal of spacer 1356 creates the access channel, as held open by retractor blades 926.

Retractor blades 926, before or after insertion via spacer 1356, are coupled to a surgical arm (e.g., surgical arm 102, 902, 1002, 1102, etc.) at an instrument connector, such as instrument connector 106. Once the retractor blades 926 are coupled to the surgical arm and positioned as desired (e.g., to hold open the access channel), joints of the surgical arm are locked (e.g., via locking mechanism 1140) to secure the retractor blades 926 in the desired position.

In some embodiments, the plurality of tubes 1354 may include grooves 1368 corresponding to grooves 1364 of spacer 1356, as shown in FIG. 18. In particular, rather than including smooth walls (e.g., circular walls, oval walls, etc.), the walls of the plurality of tubes 1354 include a plurality of grooves 1368. By including grooves 1368, rotational movement between tubes 1354 is reduced and/or eliminated. In these embodiments, initial insertion tube 1354*a* may optionally be smooth (e.g., may not include grooves 1368) to facilitate improved insertion.

Example embodiments described herein may facilitate use of an instrument connector that secures a sterile drape to a surgical arm, while at the same time, enables connection to a variety of surgical instruments. By sealing the sterile drape to the surgical arm with the instrument connector, the need for other means for securing the drape to the surgical arm (e.g., tape, etc.) is eliminated. Further, the time required to secure the drape may also be reduced. And, in some embodiments, the connection created between the surgical arm and the instrument connector may more securely retain the drape than tape or other conventional means of securing a sterile drape during surgery (e.g., elastic portions of sterile drapes). Similarly, the time required to sterilize the equipment prior to surgical use may be reduced as the sterilization of the surgical arm is achieved using the sterile drape (i.e., it is not required for the surgical arm itself to be sterilized before using the arm). Further, when the instrument connector is coupled to the socket of the surgical arm, the seal created by the instrument connector between the surgical arm and the drape eliminates contact between sterilized and non-sterilized components. This allows surgical instruments (e.g., retractor blades, etc.) attached to the instrument connector to be changed as many times as needed, without breaking the sterilized field.

Example embodiments described herein may also facilitate insertion of retractor blades having curved prongs or teeth through a percutaneous access system. By providing a spacer with a plurality of grooves for insertion into a final dilator, the prongs of the retractor blade are able to be inserted through the grooves of the spacer. Further, in some embodiments, the spacer includes a header at the top portion of the spacer, which maintains the grooves at the top of the spacer, while providing additional space towards the bottom of the spacer for insertion of curved retractor blades.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. A surgical access system comprising:
   a plurality of nesting tubes including an insertion tube of a smallest size, at least one intermediate tube of at least one intermediate size, and a final tube of a largest size, the plurality of tubes configured for sequential insertion into a patient;
   a spacer including a plurality of grooves extending along a length of the spacer, the spacer configured for insertion into the final tube of the plurality of tubes upon removal of the insertion tube and the at least one intermediate tube from the final tube; and
   at least one retractor blade having a plurality of prongs, wherein the prongs of the at least one retractor blade are configured to engage with the plurality of grooves of the spacer.

2. The surgical access system of claim 1, wherein the at least one retractor blade is configured for insertion into the patient via the grooves of the spacer when the final tube of the plurality of tubes is removed and the spacer remains inserted into the patient, whereby an access channel for surgery is created upon removal of the spacer.

3. The surgical access system of claim 1, wherein the prongs of the at least one retractor blade include a curved portion.

4. The surgical access system of claim 1, wherein the spacer includes a plurality of extensions and a header coupled between the plurality of extensions, wherein the grooves are partially defined by the plurality of extensions and the header.

5. The surgical access system of claim 4, wherein the header extends less than the full length of the spacer.

6. The surgical access system of claim 1, wherein each of the plurality of nesting tubes are of oval cross-section.

7. The surgical access system of claim 1, wherein each of the plurality of nesting tubes include a plurality of grooves corresponding to the plurality of grooves of the spacer.

* * * * *